United States Patent [19]

Beck

[11] 4,003,132
[45] Jan. 18, 1977

[54] DEVICES AND METHODS FOR TAKING DENTAL IMPRESSIONS

[76] Inventor: Joseph F. Beck, 33 Huntington Road, Newton, Mass. 02158

[22] Filed: May 19, 1975

[21] Appl. No.: 578,718

[52] U.S. Cl. .................................................. 32/17
[51] Int. Cl.² ............................................ A61C 9/00
[58] Field of Search ....................................... 32/17

[56] References Cited

UNITED STATES PATENTS 2,567,794  9/1951  Winett .................................... 32/17
3,468,029  9/1969  Moore .................................... 32/17

Primary Examiner—Robert Peshock
Attorney, Agent, or Firm—Maurice R. Boiteau

[57] ABSTRACT

There is disclosed in the present application a series of trays adapted to carrying dental impression medium of varying viscosities on both sides of a thin textile web and between lateral containing walls to permit the taking of impressions of both jaws together in one tray and with the teeth or gums positioned near their normal biting engagement. There is also included in the present disclosure a perforated plate for applying lateral pressure to the medium thereby limiting the thickness of the impression medium and improving the accuracy of that part of the impression taken from the lateral surfaces of teeth.

9 Claims, 7 Drawing Figures

DEVICES AND METHODS FOR TAKING DENTAL IMPRESSIONS

The present invention relates generally to devices and methods for taking impressions of a patient's tooth and gum surfaces for the purpose of guiding the accurate replacement of one or more teeth.

Prosthetic dentistry whether concerned with the fitting of a single crown, the replacement of one or more teeth in a bridge or a partial plate, a full upper or lower plate or both conventionally requires for the comfort of the patient, that a plurality of separate impressions be taken to assure an accurate rendition of gum surfaces and of adjacent and opposite tooth surfaces. In the process of correlating the various impressions, errors are introduced with resultant inaccuracy in the shape of the dental appliance an inclusive term employed herein for all tooth replacements or supplements unless otherwise specified. The errors arise both from a failure to obtain accurate individual impressions and also from inaccuracies in registering the various separate impressions. The result is that the patient is subjected to considerable suffering in adjusting to the new appliance and must often return several times to the dentist for fittings and in severe cases, for the replacement of the appliance based on a completely new start. In addition, even when the conventional multiple impression system yields a somewhat satisfactory appliance, the result most often is less than an optimum fit at considerable expenditure of dentist's and patient's time and accordingly in additional expense to the patient.

In order to eliminate the errors inherent in a plurality of individual impressions including those stemming from inaccurate registration, it is desirable to combine in a single tray the full impression of the teeth and/or gums of both jaws as well as the relationship of the teeth at occlusal surfaces. In addition, it is also desirable to improve the overall quality of the impression.

A general object of the invention is therefore to improve the efficiency in the taking of dental impressions and in the performance of subsequent dependent operations.

Another object is to reduce the time required of the dentist and patient for the accurate fitting of dental appliances.

Still another object is to render the dental appliance more comfortable to the patient by providing greater accuracy in its production.

The foregoing objects are achieved in accordance with the invention by a series of dental impression trays and methods, the various trays being adapted to the taking of impressions in different parts of the mouth. In accordance with one of the features of the invention, a preferred form of tray includes a fixed plate and a pressure plate, the pressure plate being connected to the fixed plate by means of a tourniquet which pulls the pressure plate closer to the fixed plate thereby applying lateral pressure to the impression medium. The pressure plate is somewhat rigid in a vertical plane while being longitudinally malleable to adapt to the shape of the patient's mouth.

According to another feature of the invention, there is interposed between the fixed and pressure plates a web, preferably woven, which coincides with the occlusal plane and supports the impression medium as the tray is being inserted into the patient's mouth.

The foregoing objects and features as well as many advantages to be derived from the invention will become obvious from the following detailed description of an illustrative embodiment taken in connection with the accompanying drawings in which.

Figure 1:
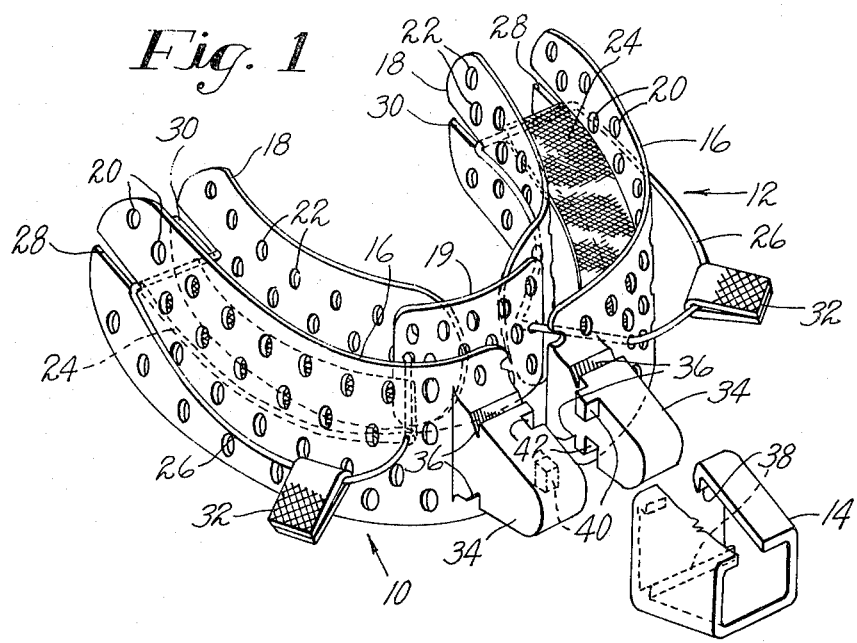
FIG. 1 is a view in perspective of two connectible half tray assemblies in accordance with the present invention.

Turning now to the drawings, particularly FIG. 1, there is shown a pair of impression tray assemblies indicated generally at 10 and 12 which may be inserted into the patient's mouth separately and then coupled together by means of a locating sleeve 14 to retain their relative orientation. The two trays 10 and 12 which are exactly alike for economy of manufacture and simplifying inventories are used respectively for the right and left sides of the patient's mouth. The tray 10 is used as the tray 12 merely by turning the tray over, bottom side up. Accordingly, the description of the structure of the tray 10 applies equally to the tray 12. The tray 10, 12 includes a curved perforated buccal plate 16 and a perforated pressure plate 18, the perforations 20 in the plate 16 and 22 in the pressure plate 18 serving to anchor the impression medium which extrudes through the perforations under the pressure of the impression. Interposed between the plates 16 and 18 is a web 24, preferably a textile web, which may be compressed laterally without increasing objectionably in thickness. The web 24 is suspended from a tourniquet 26 which passes through perforations in the forward end of the plate 16 and 18 and through slots 28 and 30 in the plates 16 and 18 respectively. Alternatively, the web 24 may be secured to the plates 16 and 18 by adhesive, for example. A key 32 which is looped over the tourniquet is wound tight and held by the patient to bring the plate 18 closer to the plate 16 and thus apply a lateral force to the impression medium after the patient has bitten down on the impression medium on the top and bottom of both trays. In the event that an impression is required only from one side of the patient's mouth, only one of the trays 10, 12 is employed. Preferably, the fixed plate 16 is of molded plastic and the pressure plate is metallic of such thickness and malleability that it is relatively stiff in a vertical plane whereas it may be formed manually to adapt to the arch of the patient's mouth in a horizontal plane. It has been found that a perforated aluminum ribbon of suitable thickness works well for this purpose.

Each of the fixed plates 16 is formed at its forward end with a bullet nosed boss 34 notched at 36 on top and bottom surfaces to receive reentrant locking flanges 38 on the sleeve 14. On the inner surfaces of the bosses 34 are formed a projection 40 and a notch 42 adapted to fit one within the other to maintain orientation of the two trays.

Figure 2:
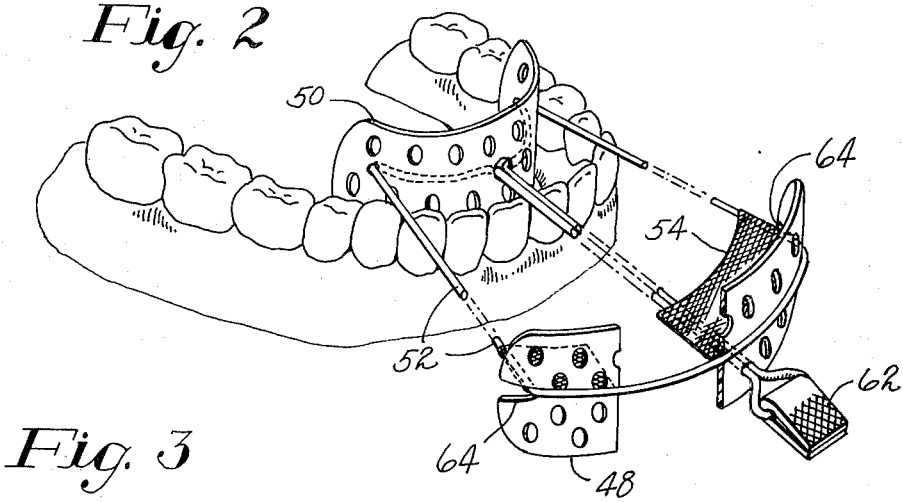
FIG. 2 is a view in perspective of a tray according to the invention especially adapted to the taking of impressions in limited areas shown being employed in the anterior portion of the mouth.
Figure 3:
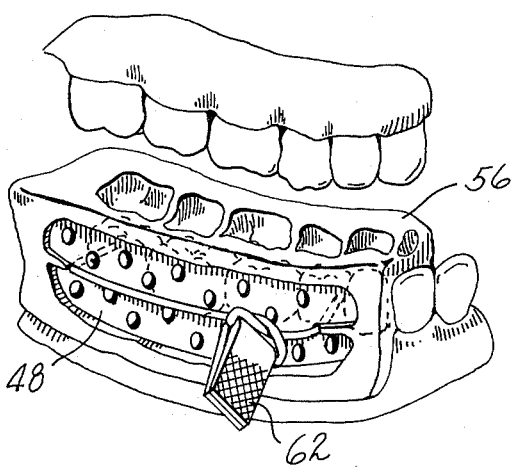
FIG. 3 is a view in perspective of the tray of FIG. 2 filled with impression medium having been used for the taking of a dental impression and shown still in the patient's mouth.
Figure 4:
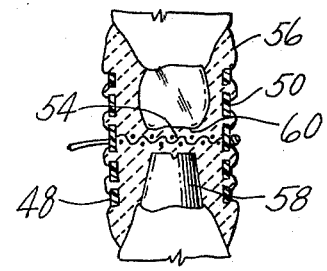
FIG. 4 is a view in transverse section showing the relationship of the teeth of both jaws in the impression medium using the tray of FIG. 3.

Shown in FIGS. 2 to 4 is a tray intended for taking dental impressions in somewhat limited areas of the mouth. The tray of FIG. 2 comprises perforated buccal and lingual plates 48 and 50 respectively, a tourniquet 52 and a web 54 suspended on the tourniquet or otherwise secured to the plates. In FIG. 2 the tray assembly is shown for clarity being applied to frontal teeth without the necessary impression medium. In FIGS. 3 and 4 the quantity of impression medium is shown for taking an impression of a plurality of upper and lower molars at the right side of the patient's mouth. As seen in FIG. 4 a tooth 58 which has been prepared to receive a crown is a part of the impression. Because the impression not only contains exactly the shape of the prepared tooth 58 and the adjacent teeth but also in the same impression shows the exact distance from the opposite tooth 60, the crown produced from this impression requires a minimum of fitting, if any.

The tray of FIGS. 2 to 4, when introduced into the patient's mouth contains a charge of impression medium, usually in modern practice a silicone putty which is applied roughly to both sides of the web 54. In order to obtain superior detail in the impression, a less viscous form of the putty is applied directly to the teeth and combines with putty during the taking of the impression thereby yielding greater definition than would otherwise be possible. After the patient has bitten down upon the impression medium, a key 62 looped over the tourniquet is turned to tighten the tourniquet which may be either a cord or a fine stainless steel wire, for example. The tourniquet 52 passes across the front of the buccal plate 48, through slots 64 in the buccal plate and through perforations in the lingual plate 50. The ends of the tourniquet are returned to the key 62 through central perforations in the two plates.

Figure 5:
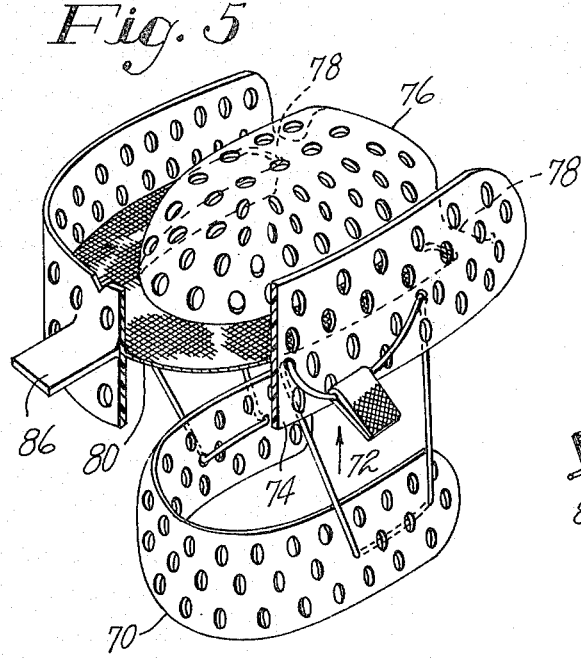
FIG. 5 is a view in perspective of a combination tray intended for taking full impressions of both jaws simultaneously.
Figure 6:
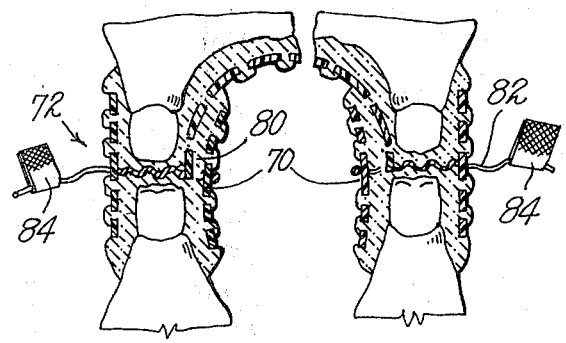
FIG. 6 is a view in transverse section of the tray of FIG. 5 in approximately the position that it occupies in the patient's mouth during the taking of an impression.

There is shown in FIGS. 5 and 6 a single tray for taking full upper and lower impressions simultaneously while having the benefit of applying lateral pressure by means of a single arcuate pressure plate 70. In addition to the plate 70, the assembly depicted in FIGS. 5 and 6 comprises a unitary moulding indicated generally at 72 formed to include a perforated buccal plate 74 and a palatal form 76 by bridges 78 at the rearward ends to the buccal plate. A web 80 is mounted in a horizontal plane between the buccal plate 74 and the palatal form 76. Typically the web 80 may be cemented to the plate 74 and suspended on the strand of each of two tourniquets 82, each provided with a key 84. The tourniquets 82 are connected between the rearward ends of the pressure plate 70 and the buccal plate 74 in such a way that tightening the tourniquets not only brings the rearward ends of the pressure plate and the buccal plate closer together but also biases the central portion of the pressure plate forwardly in the process.

Figure 7:
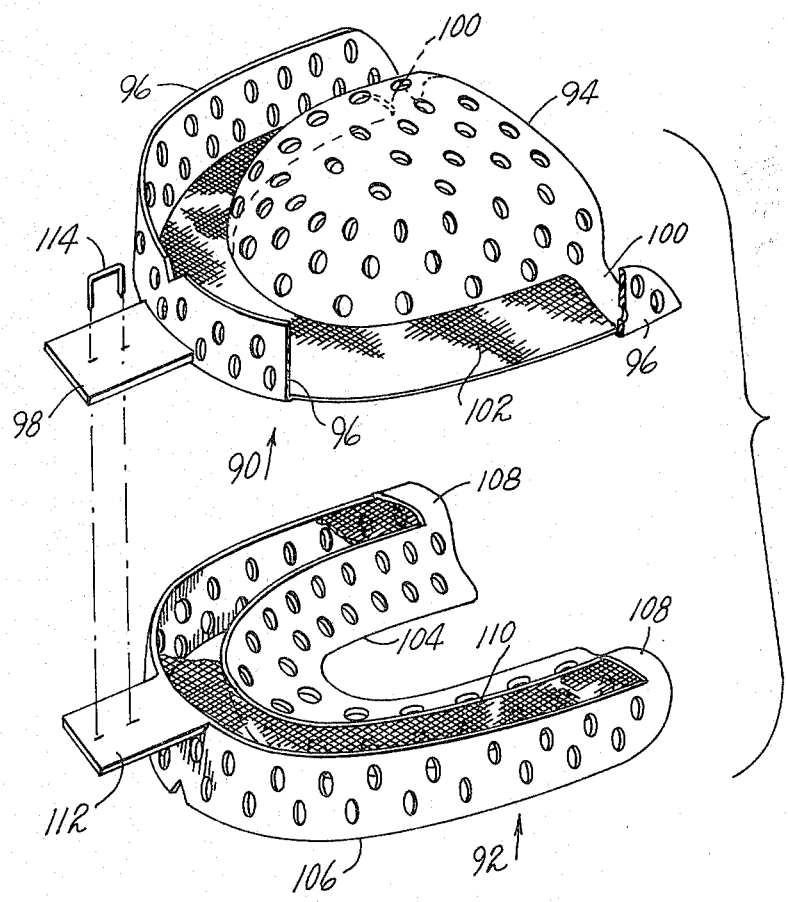
FIG. 7 is a view in perspective of full upper and lower trays with means for coupling the trays together so as to retain the registration between the combined impressions taken sequentially but removed together from the patient's mouth.

Shown in FIG. 7 is a pair of trays used for taking full impressions of upper and lower jaws successively but intended to be taken out together after the registration of the two impressions has been established. The showing of FIG. 7 comprises an upper tray indicated generally at 90 and a lower tray indicated generally at 92. The tray 90 comprises a central perforated palate form 94 and a peripheral rim 96 on which is formed a thin handle 98. The palate form 94 and the rim 98 are joined at their rearward ends by bridges 100 and a web 102 extends about the entire periphery between the palate form and rim from bridge to bridge. The lower tray 92 comprises lingual and buccal arcuate rims 104 and 106 respectively connected at their rearward ends by bridges 108. Between the upper edges of the rims 104 and 106 is a web 110 extending from one of the bridges 108 around to the other. Like the tray 90, the tray 92 is preferably an integral plastic molding and includes a thin handle 112. After impressions have been taken first in one tray and then in the other, the handles 98 and 112 are joined together by a staple 114 to retain the relative orientation of the two trays as they are being pulled out together from the patient's mouth. The orientation of the two impressions is also maintained by the impression medium which flows through the webs 102 and 110 and in effect merges the medium in the two trays into one, thereby assisting in orienting the two full impressions in a pair of interconnected trays.

The tray assemblies already described in which a pair of relatively movable plates are interconnected by a tourniquet yield greater detail in dental impressions than would otherwise be possible. Because the impression medium is laterally contained at the same time that the patient's bite is applying pressure to the medium vertically, the medium is subjected to hydraulic pressure in all directions thereby flowing with greater force toward the teeth or gums to obtain the greater definition in the impression than would result from the use of conventional devices and methods. The thin web occurring in the occlusal plane in using the various forms of trays serves to retain the roughly formed charge of impression medium but is thin enough to permit the patient to bite down bringing the teeth close to contact and producing an impression in the medium which closely corresponds to normal occlusion. This bite condition is the basis of a superior dental appliance from the point of view of the patient's adjustment and comfort.

Having thus disclosed my invention, what I claim as new and desire to secure by Letters Patent of the United States is:

1. A tray assembly for taking a dental impression in a patient's mouth in an impression medium contained in the tray assembly comprising buccal and lingual plates each relatively rigid to resist deformation in a vertical plane by the hydraulic pressure of the medium while in the patient's mouth when the patient bites down upon the medium but sufficiently bendable to adapt to the contour of the patient's arch, flexible strand means interconnecting the two plates for forcing the plates closer together to apply lateral pressure to the medium and a medium supporting means including a web interposed between the lingual and buccal plates and positioned to coincide with the patient's occlusal plane.

2. A tray assembly according to claim 1 further characterized in that the flexible strand means is in the form of a tourniquet interconnecting the two plates (the two plates are interconnected by a tourniquet and) which are relatively (movable) pressed toward one another as the tourniquet is manually tightened.

3. A tray assembly according to claim 2 in which the plates are perforated to provide multiple anchor points for the impression medium.

4. A plate assembly according to claim 1 further characterized in that one of the plates is of perforated metal relatively rigid in a vertical plane but deformable in a horizontal plane to accommodate to the shape of the patient's mouth.

5. A tray according to claim 2 further characterized in that both plates are of perforated metal.

6. A tray assembly according to claim 5 further characterized in that the two plates are short in a horizontal direction but of a width extending from one gum line to the other to adapt to taking an impression in a limited area of the patient's mouth.

7. A method of taking a dental impression comprising the steps of applying to a desired area of a patient's mouth a quantity of impression putty contained in a tray having a web positioned to coincide with the patient's occlusal plane, the tray also comprising laterally movable buccal and lingual plates of sufficient stiffness to resist deformation under the pressure of the impression, directing the patient to bite down on the medium, (and) bringing the plates closer together to form the impression and securing them in position while removing the impression putty and tray together from the patient's mouth.

8. A method according to claim 7 comprising the further step of applying directly to the patient's teeth a coating of a less viscous form of the putty which thereafter merges with the putty in the tray.

9. A tray assembly for taking a dental impression in a patient's mouth in an impression medium contained in the tray assembly comprising buccal and lingual plates each relatively rigid to resist deformation in a vertical plane by the hydraulic pressure of the medium while in the patient's mouth when the patient bites down upon the medium but sufficiently bendable to adapt to the contour of the patient's arch, flexible strand means interconnecting the two plates for urging the plates closer together to apply lateral pressure to the medium and means for supporting the impression medium on the plates as the tray assembly is inserted into and removed from the patient's mouth.

* * * * *